(12) United States Patent
Carlson et al.

(10) Patent No.: US 8,277,389 B2
(45) Date of Patent: *Oct. 2, 2012

(54) SENSING RATE OF CHANGE OF PRESSURE IN THE LEFT VENTRICLE WITH AN IMPLANTED DEVICE

(75) Inventors: Gerrard M. Carlson, Champlin, MN (US); Krzysztof Z. Siejko, Maple Grove, MN (US); Ramesh Wariar, Blaine, MN (US); Marina V. Brockway, Shoreview, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/178,945

(22) Filed: Jul. 8, 2011

(65) Prior Publication Data
US 2011/0263988 A1    Oct. 27, 2011

Related U.S. Application Data

(63) Continuation of application No. 12/703,533, filed on Feb. 10, 2010, now Pat. No. 8,007,442, which is a continuation of application No. 11/142,851, filed on Jun. 1, 2005, now Pat. No. 7,670,298.

(51) Int. Cl.
*A61B 5/02* (2006.01)
(52) U.S. Cl. .................. 600/528; 607/17; 607/18
(58) Field of Classification Search ............ 600/528
See application file for complete search history.

(56) References Cited

U.S. PATENT DOCUMENTS

| | | | |
|---|---|---|---|
| 4,094,308 A | 6/1978 | Cormier | |
| 4,289,141 A | 9/1981 | Cormier | |
| 4,446,872 A | 5/1984 | Marsoner et al. | |
| 4,548,204 A | 10/1985 | Groch et al. | |
| 4,649,930 A | 3/1987 | Groch et al. | |
| 4,763,646 A | 8/1988 | Lekholm | |
| 4,905,706 A | 3/1990 | Duff et al. | |
| 4,915,113 A | 4/1990 | Holman | |
| 4,989,611 A | 2/1991 | Zanetti et al. | |
| 5,159,932 A | 11/1992 | Zanetti et al. | |
| 5,365,932 A | 11/1994 | Greenhut | |
| 5,496,361 A | 3/1996 | Moberg et al. | |
| 5,554,177 A | 9/1996 | Kieval et al. | |
| 5,609,612 A | 3/1997 | Plicchi et al. | |
| 5,674,256 A | 10/1997 | Carlson | |

(Continued)

OTHER PUBLICATIONS

"U.S. Appl. No. 12/634,277, Non Final Office Action mailed Mar. 2, 2012", 10 pgs.

(Continued)

*Primary Examiner* — Carl H. Layno
*Assistant Examiner* — Jon-Eric C. Morales
(74) *Attorney, Agent, or Firm* — Schwegman Lundberg & Woessner, P.A.

(57) ABSTRACT

An implantable device and method for monitoring S1 heart sounds with a remotely located accelerometer. The device includes a transducer that converts heart sounds into an electrical signal. A control circuit is coupled to the transducer. The control circuit is configured to receive the electrical signal, identify an S1 heart sound, and to convert the S1 heart sound into electrical information. The control circuit also generates morphological data from the electrical information. The morphological data relates to a hemodynamic metric, such as left ventricular contractility. A housing may enclose the control circuit. The housing defines a volume coextensive with an outer surface of the housing. The transducer is in or on the volume defined by the housing.

20 Claims, 6 Drawing Sheets

U.S. PATENT DOCUMENTS

| | | | |
|---|---|---|---|
| 5,685,317 A | 11/1997 | Sjostrom | |
| 5,687,738 A | 11/1997 | Shapiro et al. | |
| 5,697,375 A | 12/1997 | Hickey | |
| 5,700,283 A | 12/1997 | Salo | |
| 5,738,102 A | 4/1998 | Lemelson | |
| 5,792,195 A | 8/1998 | Carlson et al. | |
| 5,836,987 A | 11/1998 | Baumann et al. | |
| 5,853,005 A | 12/1998 | Scanlon | |
| 5,991,661 A | 11/1999 | Park et al. | |
| 6,009,349 A | 12/1999 | Mouchawar et al. | |
| 6,026,324 A | 2/2000 | Carlson | |
| 6,044,298 A | 3/2000 | Salo et al. | |
| 6,044,299 A | 3/2000 | Nilsson | |
| 6,045,513 A | 4/2000 | Stone et al. | |
| 6,053,872 A | 4/2000 | Mohler | |
| 6,058,329 A | 5/2000 | Salo et al. | |
| 6,064,910 A | 5/2000 | Andersson et al. | |
| 6,077,227 A | 6/2000 | Miesel | |
| 6,152,884 A | 11/2000 | Bjorgaas | |
| 6,264,611 B1 | 7/2001 | Ishikawa et al. | |
| 6,298,269 B1 | 10/2001 | Sweeney | |
| 6,312,378 B1 | 11/2001 | Bardy | |
| 6,366,811 B1 | 4/2002 | Carlson | |
| 6,368,283 B1 | 4/2002 | Xu et al. | |
| 6,409,675 B1 | 6/2002 | Turcott | |
| 6,415,033 B1 | 7/2002 | Halleck et al. | |
| 6,440,078 B1 | 8/2002 | Curiel et al. | |
| 6,440,082 B1 | 8/2002 | Joo et al. | |
| 6,477,406 B1 | 11/2002 | Turcott | |
| 6,491,639 B1 | 12/2002 | Turcott | |
| 6,527,729 B1 | 3/2003 | Turcott | |
| 6,575,916 B2 | 6/2003 | Halleck et al. | |
| 6,643,548 B1 | 11/2003 | Mai et al. | |
| 6,650,940 B1 | 11/2003 | Zhu et al. | |
| 6,665,564 B2 | 12/2003 | Lincoln et al. | |
| 6,795,732 B2 | 9/2004 | Stadler et al. | |
| 6,810,287 B2 | 10/2004 | Zhu et al. | |
| 6,824,519 B2 | 11/2004 | Narimatsu et al. | |
| 6,830,548 B2 | 12/2004 | Bonnet et al. | |
| 6,839,593 B1 | 1/2005 | Sun et al. | |
| 6,845,263 B2 | 1/2005 | Kawaguchi | |
| 6,963,777 B2 | 11/2005 | Lincoln et al. | |
| 7,039,462 B2 | 5/2006 | Pastore et al. | |
| 7,052,466 B2 | 5/2006 | Scheiner et al. | |
| 7,079,896 B1 | 7/2006 | Park et al. | |
| 7,115,096 B2 | 10/2006 | Siejko et al. | |
| 7,123,962 B2 | 10/2006 | Siejko et al. | |
| 7,174,203 B2 | 2/2007 | Arand et al. | |
| 7,634,309 B2 | 12/2009 | Wariar et al. | |
| 7,670,298 B2 * | 3/2010 | Carlson et al. | 600/528 |
| 8,007,442 B2 * | 8/2011 | Carlson et al. | 600/528 |
| 2002/0001390 A1 | 1/2002 | Kawaguchi | |
| 2002/0035337 A1 | 3/2002 | Oka | |
| 2002/0082645 A1 | 6/2002 | Sweeney | |
| 2002/0091332 A1 | 7/2002 | Bombardini | |
| 2002/0107450 A1 | 8/2002 | Ogura | |
| 2002/0147401 A1 | 10/2002 | Oka | |
| 2002/0151812 A1 | 10/2002 | Scheiner et al. | |
| 2002/0151938 A1 | 10/2002 | Corbucci | |
| 2002/0188329 A1 | 12/2002 | Struble | |
| 2003/0055352 A1 | 3/2003 | Hayek et al. | |
| 2003/0055461 A1 | 3/2003 | Girouard et al. | |
| 2003/0069608 A1 | 4/2003 | Sweeney | |
| 2003/0072458 A1 | 4/2003 | Halleck et al. | |
| 2003/0093002 A1 | 5/2003 | Kuo | |
| 2003/0093003 A1 | 5/2003 | Watrous et al. | |
| 2003/0120159 A1 | 6/2003 | Mohler | |
| 2003/0176896 A1 | 9/2003 | Lincoln et al. | |
| 2003/0208240 A1 | 11/2003 | Pastore et al. | |
| 2003/0216620 A1 | 11/2003 | Jain et al. | |
| 2003/0229289 A1 | 12/2003 | Mohler | |
| 2004/0024423 A1 | 2/2004 | Lincoln et al. | |
| 2004/0039419 A1 | 2/2004 | Stickney et al. | |
| 2004/0039420 A1 | 2/2004 | Jayne et al. | |
| 2004/0064056 A1 | 4/2004 | Ogura | |
| 2004/0078059 A1 | 4/2004 | Ding et al. | |
| 2004/0078060 A1 | 4/2004 | Ding et al. | |
| 2004/0106874 A1 | 6/2004 | Eigler et al. | |
| 2004/0106960 A1 | 6/2004 | Siejko et al. | |
| 2004/0106961 A1 | 6/2004 | Siejko et al. | |
| 2004/0127792 A1 | 7/2004 | Siejko et al. | |
| 2004/0138572 A1 | 7/2004 | Thiagarajan | |
| 2004/0167417 A1 | 8/2004 | Schulhauser et al. | |
| 2004/0204744 A1 | 10/2004 | Penner et al. | |
| 2004/0215264 A1 | 10/2004 | Van Bentem | |
| 2004/0225332 A1 | 11/2004 | Gebhardt et al. | |
| 2004/0230129 A1 | 11/2004 | Haefner | |
| 2004/0236239 A1 | 11/2004 | Murray et al. | |
| 2004/0254481 A1 | 12/2004 | Brodnick | |
| 2004/0254483 A1 | 12/2004 | Zdeblick et al. | |
| 2004/0267147 A1 | 12/2004 | Sullivan | |
| 2004/0267148 A1 | 12/2004 | Arand et al. | |
| 2005/0010257 A1 | 1/2005 | Lincoln et al. | |
| 2005/0027323 A1 | 2/2005 | Mulligan et al. | |
| 2005/0033190 A1 | 2/2005 | Bauer | |
| 2005/0102001 A1 | 5/2005 | Maile et al. | |
| 2005/0119708 A1 | 6/2005 | Haefner | |
| 2006/0020294 A1 | 1/2006 | Brockway et al. | |
| 2006/0048894 A1 | 3/2006 | Yamazaki et al. | |
| 2006/0122651 A1 | 6/2006 | Whitman | |
| 2006/0167334 A1 | 7/2006 | Anstadt et al. | |
| 2006/0247702 A1 | 11/2006 | Stegemann et al. | |
| 2006/0276849 A1 | 12/2006 | Carlson et al. | |
| 2006/0282000 A1 | 12/2006 | Zhang et al. | |
| 2007/0043299 A1 | 2/2007 | Wariar et al. | |
| 2010/0087890 A1 | 4/2010 | Wariar et al. | |
| 2010/0145403 A1 | 6/2010 | Carlson et al. | |

OTHER PUBLICATIONS

"U.S. Appl. No. 11/142,851, Examiner Interview Summary filed Dec. 23, 2008", 1 pg.

"U.S. Appl. No. 11/142,851, Final Office Action mailed Jul. 15, 2008", 7 pgs.

"U.S. Appl. No. 11/142,851, Final Office Action mailed Oct. 6, 2008", 7 pgs.

"U.S. Appl. No. 11/142,851, Non-Final Office Action mailed Feb. 7, 2008", 6 pgs.

"U.S. Appl. No. 11/142,851, Non-Final Office Action mailed May 18, 2007", 7 pgs.

"U.S. Appl. No. 11/142,851, Non-Final Office Action mailed May 21, 2009", 7 pgs.

"U.S. Appl. No. 11/142,851, Non-Final Office Action mailed Dec. 19, 2008", 6 pgs.

"U.S. Appl. No. 11/142,851, Notice of Allowance mailed Sep. 27, 2007", 7 pgs.

"U.S. Appl. No. 11/142,851, Notice of Allowance mailed Oct. 6, 2009", 6 pgs.

"U.S. Appl. No. 11/142,851, Response filed Mar. 2, 2009 to Non-Final Office Action mailed Dec. 19, 2008", 7 pgs.

"U.S. Appl. No. 11/142,851, Response filed May 7, 2008 to Non-Final Office Action mailed Feb. 7, 2008", 8 pgs.

"U.S. Appl. No. 11/142,851, Response filed Jun. 23, 2009 to Non-Final Office Action mailed May 21, 2009", 15 pgs.

"U.S. Appl. No. 11/142,851, Response filed Aug. 16, 2007 to Non-Final Office Action mailed May 18, 2007", 17 pgs.

"U.S. Appl. No. 11/208,281, Examiner Interview Summary mailed Jan. 29, 2009", 4 pgs.

"U.S. Appl. No. 11/208,281, Final Office Action mailed May 14, 2008", 10 pgs.

"U.S. Appl. No. 11/208,281, Non-Final Office Action mailed Aug. 10, 2007", 9 pgs.

"U.S. Appl. No. 11/208,281, Non-Final Office Action mailed Oct. 28, 2008", 13 pgs.

"U.S. Appl. No. 11/208,281, Notice of Allowance mailed Aug. 4, 2009", 7 pgs.

"U.S. Appl. No. 11/208,281, Response filed Mar. 3, 2008 to Restriction Requirement mailed Jan. 31, 2008", 11 pgs.

"U.S. Appl. No. 11/208,281, Response filed May 7, 2009 to Restriction Requirement mailed Apr. 16, 2009", 8 pgs.

"U.S. Appl. No. 11/208,281, Response filed Aug. 14, 2008 to Final Office Action mailed May 14, 2008", 19 pgs.

"U.S. Appl. No. 11/208,281, Response filed Jan. 28, 2009 to Non Final Office Action mailed Oct. 28, 2008", 13 pgs.

"U.S. Appl. No. 11/208,281, Response filed Nov. 13, 2007 to Non-Final Office Action mailed Aug. 10, 2007", 44 pgs.

"U.S. Appl. No. 11/208,281, Restrictio Requirement mailed Jan. 31, 2008", 8 pgs.

"U.S. Appl. No. 11/208,281, Restriction Requirement mailed Apr. 16, 2009", 6 pgs.

"U.S. Appl. No. 12/703,533, Non-Final Office Action mailed Oct. 1, 2010", 7 pgs.

"U.S. Appl. No. 12/703,533, Notice of Allowance mailed Mar. 24, 2011", 7 pgs.

"U.S. Appl. No. 12/703,533, Notice of Allowance mailed Dec. 7, 2010", 4 pgs.

"U.S. Appl. No. 12/703,533, Preliminary Amendment filed Mar. 3, 2011", 9 pgs.

"U.S. Appl. No. 12/703,533, Response filed Oct. 25, 2010 to Non Final Office Action mailed Oct. 1, 2010", 13 pgs.

Bongiorni, M. G, et al., "Is local myocardial contractility related to endocardial acceleration signals detected by a transvenous pacing lead?", Pacing Clin Electrophysiol, (11 Pt 2), (Nov. 1996), 1682-1688.

Jaski, B. E., "Chapter 3—Circulation, Part 1: The Problem of Heart Failure", Basics of Heart Failure: A Problem Solving Approach, Kluwer Academic Publishers, Norwell, MA, (2000), 25-52.

Little, William C, et al., "Assessment of Normal and Abnormal Cardiac Function", Heart Disease: A Textbook of Cardiovascular Medicine, W.B. Saunders, Philadelphia PA, (2001), 479-502.

Wariar, Ramesh, et al., "Tracking Progression of Congestive Heart Failure Via a Force-Frequency Relationship", U.S. Appl. No. 11/208,281, filed Aug. 19, 2005, 41 pgs.

* cited by examiner

SENSING RATE OF CHANGE OF PRESSURE IN THE LEFT VENTRICLE WITH AN IMPLANTED DEVICE

CROSS REFERENCE TO RELATED APPLICATIONS

This application is a continuation of U.S. application Ser. No. 12/703,533, filed Feb. 10, 2010, now issued as U.S. Pat. No. 8,007,442, which is a continuation of U.S. application Ser. No. 11/142,851, filed Jun. 1, 2005, now issued as U.S. Pat. No. 7,670,298, which is hereby incorporated by reference in its entirety.

TECHNICAL FIELD

This document relates to cardiac rhythm management devices generally, and more particularly to cardiac rhythm management devices that employ a sensing device to detect a heart sound and to extract morphological data therefrom, in order to relate the heart sound to a hemodynamic metric.

BACKGROUND

Cardiac pacemakers generally provide functions including sensing electrical signals generated by the heart, controlling stimulation of excitable tissues in the heart, sensing the response of the heart to such stimulation, and responding to inadequate or inappropriate stimulus or response (e.g., dysrhythmia) to deliver therapeutic stimuli to the heart. Some pacemakers employ cardiac resynchronization therapy. Some existing cardiac pacemakers also function to communicate with an external programmer device to support a variety of monitoring, diagnostic and configuration functions.

Certain cardiac pacemakers, defibrillators with pacing and/or cardiac resynchronization therapy (CRT) capabilities, and CRT devices (collectively referred to herein by the term "pacemaker") include an internal accelerometer for measuring the level of activity of the patient (e.g., movement caused by walking around, or by muscle twitches). Such pacemakers process (e.g., filter) the accelerometer signal to reduce noise interfering with the measurement of the patient's motion-related activity, such as the sounds generated by the heart itself, and then use the processed signals as inputs to one or more algorithms for generating the signals used to control the stimulation of the heart. For example, if the accelerometer indicates that a patient is walking briskly, the pacemaker may stimulate the heart to beat at a faster rate (often subject to an upper rate limit) than when the patient is at rest.

Pacemakers are typically electrically coupled to a patient's heart by a lead system. The lead system may include one or multiple leads that may provide electrical contact with one or multiple chamber of a patient's heart. Some leads may contain an accelerometer at their distal end. When implanted, the accelerometer is located within a patient's heart, and may detect sounds emitted by the heart. Such a scheme may be used, for example, to detect an S1 heart sound (an S1 heart sound is the first sound made by the heart during a cardiac cycle). It is known that an S1 heart sound contains data content related to left ventricular contractility, a characteristic of the heart that reveals the capacity of the myocardium to shorten, and therefore to circulate blood through the body. A pacemaker system such as the one described may measure S1 heart sounds as a means to gather information about the contractility of the patient's heart.

The above-described scheme exhibits certain shortcomings, however. Such a scheme may lead to the use of two accelerometers—an internal accelerometer for use in adjusting the pacing rate during instances of physical exertion by the patient, and an external accelerometer situated in the heart for the purpose of monitoring heart sounds. Disposing an accelerometer on the tip of a lead is costly, and could be avoided if an internal accelerometer could be used to detect heart sounds with a sufficient signal-to-noise ratio to permit extraction of data content related to cardiac performance (such as left ventricular contractility).

SUMMARY

Against this backdrop the present invention was developed. According to one embodiment, an implantable device includes a transducer that converts heart sounds into an electrical signal. A control circuit is coupled to the transducer. The control circuit is configured to receive the electrical signal, identify an S1 heart sound, and convert the S1 heart sound into morphological data that relates to a rate of change of pressure within a ventricle of a heart. A housing encloses the control circuit. The transducer is located in a region in or on the housing.

According to another embodiment, a method includes using a transducer located outside of a heart to detect an S1 heart sound. The S1 heart sound is converted into an electrical signal using the transducer. Morphological data is extracted from the electrical signal. The morphological data relates to a rate of change of pressure within a ventricle of the heart.

According to yet another embodiment, a system includes an implantable device and an external system. The implantable device includes a transducer located in or on the implantable device. The transducer is configured to convert heart sounds into an electrical signal. A first control circuit is coupled to the transducer, and is configured to receive the electrical signal. The implantable device also includes a first interface circuit for communicating with the external system. The external system includes a second interface circuit for communicating with the implantable device. A second control circuit is coupled to the second interface circuit. The first and second control circuits cooperate to identify an S1 heart sound, and to generate morphological data from the S1 heart sound. The morphological data relates to a rate of change of pressure in a ventricle of a heart.

DETAILED DESCRIPTION

During the course of a cardiac cycle, blood flows from the peripheral venous system to the right atrium. From the right atrium, blood passes through the tricuspid valve to the right ventricle. Blood exits the right ventricle, through the pulmonic valve, into the pulmonary artery, and is directed through the lungs, so that the blood may be reoxygenated. Oxygenated blood from the lungs is drawn from the pulmonary vein to the left atrium. From the left atrium, blood passes though the mitral valve to the left ventricle. Finally, the blood flows from the left ventricle, through the aortic valve, to the peripheral arterial system in order to transfer oxygenated blood to the organs of the body.

As the blood circulates and the various valves open and close (as just described), certain heart sounds are produced. The heart sounds occur in a fixed sequence and are respectively referred to as S1, S2, S3 and S4.

The S1 heart sound is caused by acceleration and deceleration of blood, and closure of the mitral and tricuspid valves. The S1 heart sound generated during a given cardiac cycle exhibits morphological characteristics that relate to the maximum rate of change of pressure in the left ventricle during the given cardiac cycle. The maximum rate of change of pressure in the left ventricle is related to, and may be used as a proxy measurement for, left ventricular contractility. Left ventricular contractility is important, because it indicates the capacity of the left ventricle to contract, and therefore to circulate blood through the peripheral arterial system.

Figure 1:
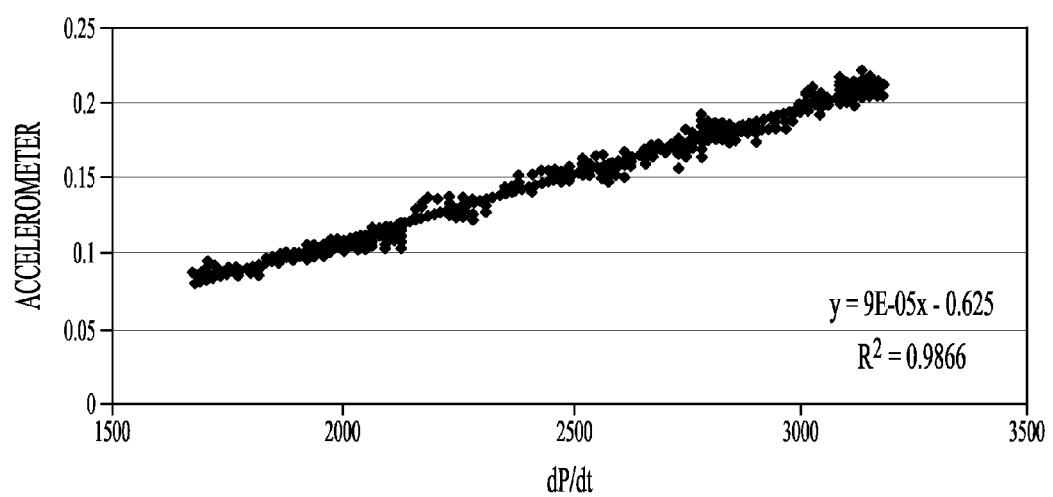
FIG. 1 depicts data supporting the notion that the S1 heart sound contains certain data content related to maximum rate of change of left ventricular pressure.

FIG. 1 depicts data illustrating that the S1 heart sound contains certain data content related to maximum rate of change of left ventricular pressure. FIG. 1 presents a chart having an x-axis and a y-axis. Maximum rate of change of left ventricular pressure for a given cardiac cycle is measured along the x-axis in units of millimeters of mercury per second (mmHg/s). Median peak-to-peak amplitude exhibited by S1 heart sounds over the past N cardiac cycles is measured along the y-axis in units of mG, where N is on the order of 10, for example, between 5 and 25. (One scheme by which "median peak-to-peak amplitude" is determined is discussed below).

To obtain the data presented in FIG. 1, animal testing was performed. During the test, the animal was at rest, and its left ventricular filling pressure was monitored and determined to be constant. Over a span of time, a drug known to modify myocardial contractility was administered. At intervals, the animal's maximum rate of left ventricular pressure change was measured, and was mated with the median peak-to-peak amplitude exhibited by S1 heart sounds over the past N=approximately 10 (5-25) cardiac cycles, as measured by an accelerometer located at a point remote from the animal's heart. (The accelerometer was located within a cardiac rhythm management device implanted in the animal). Further, the accelerometer data was signal conditioned (discussed below) prior to measurement of the peak-to-peak amplitude. Thus, a given data point on the chart of FIG. 1 is determined by the maximum rate of left ventricular pressure change during a given cycle, and the median peak-to-peak amplitude exhibited by S1 heart sounds over the past N cardiac cycles.

As can be seen from FIG. 1, the median peak-to-peak amplitude exhibited over a span of cardiac cycles increases (approximately linearly) with the maximum rate of left ventricular pressure change. Therefore, by measuring the median peak-to-peak amplitude exhibited over a span of N cardiac cycles, the maximum rate of left ventricular pressure change may be determined.

Figure 2:
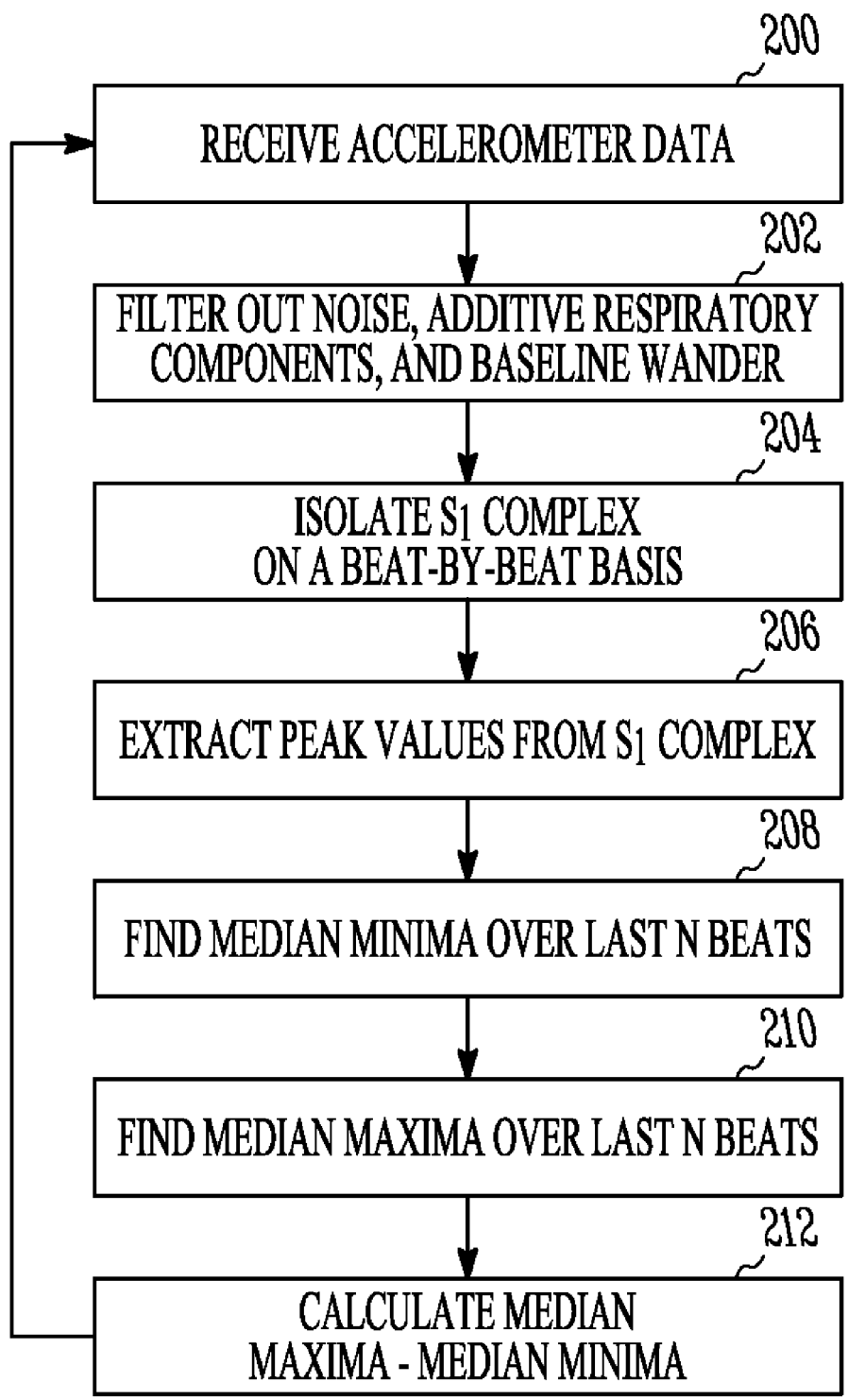
FIG. 2 depicts a method of analyzing accelerometer data to determine a morphological characteristic related to a hemodynamic metric, according to some embodiments of the present invention.

Accordingly, FIG. 2 illustrates a method useful in arriving at data indicative of left ventricular contractility. The example of FIG. 2 begins with the reception of raw accelerometer data, as shown in operation 200. Thereafter, the raw accelerometer data is conditioned (discussed below), for example, to remove noise, respiratory components, and baseline wander (operation 202). The resulting data stream substantially represents the sounds emitted by the heart.

Figure 3A:
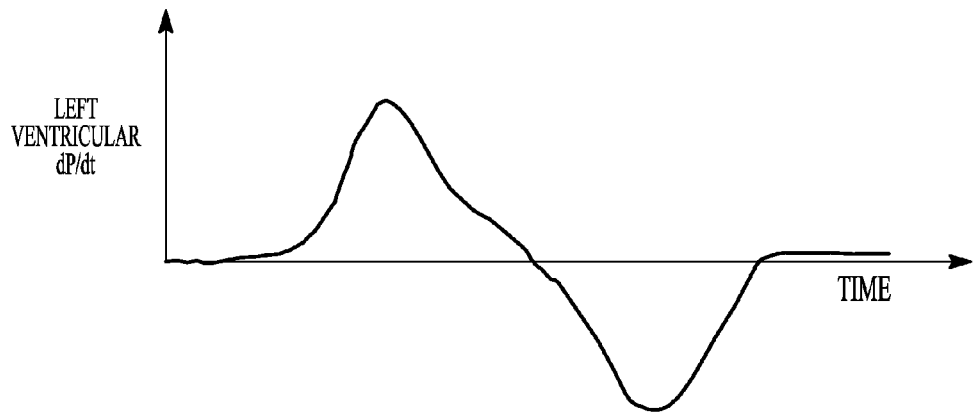
FIG. 3A depicts a chart presenting rate of change in left ventricular pressure (y-axis) versus time (x-axis).
Figure 3B:
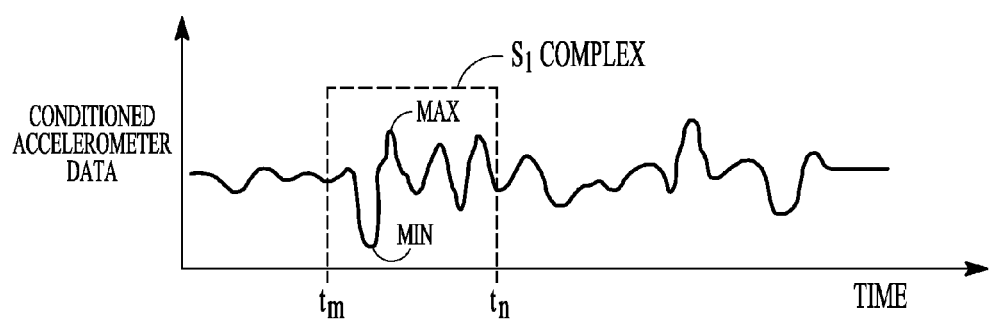
FIG. 3B depicts a chart presenting conditioned accelerometer data (y-axis) versus time (x-axis).

This conditioned signal is then processed so as to isolate the S1 complex, as shown in operation 204. The result of such a process is depicted in FIG. 3B. FIG. 3B presents conditioned accelerometer data (y-axis) versus time (x-axis). FIG. 3A presents rate of change in left ventricular pressure (y-axis) versus time (x-axis).

FIG. 3B contains a region identified by a dashed box. The dashed box identifies the S1 complex. The process of isolating the S1 complex refers to identifying a point in time $t_m$ at which the S1 complex begins, and a point in time $t_n$ at which the S1 complex ends.

Returning to FIG. 2, after isolation of the S1 complex at operation 204, peak values are extracted at operation 206. For example, the exemplary isolated S1 complex depicted in FIG. 3B contains a global maxima labeled "Max," and a global minima labeled "Min." The minima and maxima are "global" over the span of time between $t_m$ and $t_n$. The combined result of operations 200-206 is that, for each cardiac cycle, the amplitude values at each global maxima and minima exhibited by an S1 heart sound are extracted and stored in a manner to preserve their relationship to the cardiac cycle from which they were extracted.

Next, in operations 208 and 210, the median minima and the median maxima exhibited over the last N cardiac cycles are found. For example, assuming that the peak values had been extracted from the $J^{th}$ cardiac cycle in a given instance of execution of operation 206, then operations 208 and 210 yield the median minima and the median maxima exhibited over cardiac cycles J−N+1 through J.

Finally, in operation 212, the median minima determined in operation 208 is subtracted from the median maxima determined in operation 210. The result of operation 212 is an example of a "median peak-to-peak-amplitude," as referred to above with reference to FIG. 1.

Figure 4:
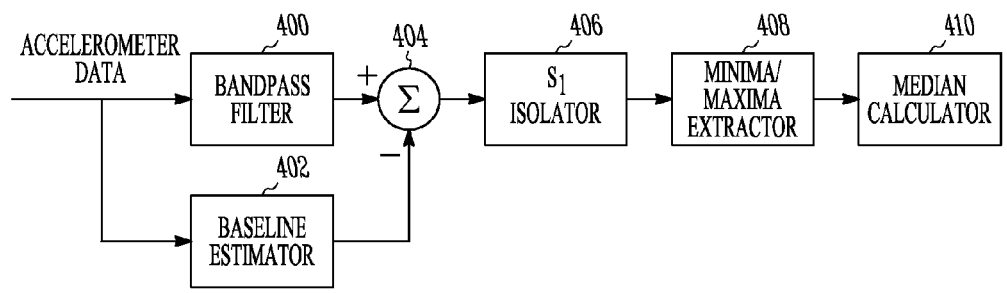
FIG. 4 depicts a signal flow scheme that may be used to implement the method of FIG. 2, according to some embodiments of the present invention.

FIG. 4 depicts a signal flow scheme that may be used to implement the method of FIG. 2. As can be seen from FIG. 4, raw accelerometer data is supplied to both a bandpass filter 400 and a baseline estimator 402. The bandpass filter 400 is characterized by upper and lower cutoff frequencies that are set to pass frequency content included in heart sounds. In one example, the lower and upper cutoff frequencies are approximately 10 Hz and 50 Hz, respectively. The cutoff frequencies are also set to reject frequency content due to movement of the patient (e.g., walking or muscular twitching), and to pass frequency content of the heart sounds.

Typically, the upper and lower cutoff frequencies of a bandpass filter (such as bandpass filter 400) are determined by two sets of poles. A first set of poles determines the lower cutoff frequency (e.g., placement of poles at 10 Hz generates a lower cutoff frequency at approximately 10 Hz). Similarly, a second set of poles determines the upper cutoff frequency (again, placement of poles at 50 Hz generates an upper cutoff frequency at approximately 50 Hz). In order to yield a narrow passband region, the sets of poles determining the upper and lower cutoff frequencies may be oriented in proximity to one another (i.e., the poles may be "squeezed" together). Unfortunately, such an approach tends to exhibit a drawback: the filter may ring when driven by signals with sharp transitions. Since S1 heart sounds tend to exhibit sharp transitions, the bandpass filter 400 may ring if its passband is narrowed by way of "squeezing" its poles close together.

To address the problem of ringing, the baseline estimator 402 is introduced. The baseline estimator 402 yields an estimate of a low-frequency baseline upon which the heart sounds in the accelerometer data are riding. For example, baseline estimator 402 may be an exponentially-weighted historical averaging unit. By subtracting the baseline estimate yielded by the estimator 402 from the output of the bandpass filter 400 (using the subtracting unit 404), unwanted low-frequency content is removed from the signal passed by the filter 400. This means that the lower cutoff frequency of the filter 400 may be relaxed (i.e., set at a relatively lower frequency), and that the combined functioning of the baseline estimator 402 and subtraction unit 404 will remove low frequency content. By relaxing the lower cutoff frequency of the filter, the frequency space between the sets of poles may also be broadened, diminishing the likelihood of ringing in the filter 400.

The combined functioning of passband filter 400, baseline estimator 402, and subtraction unit 404 operate to achieve the effect described with reference to operation 202 in FIG. 2. Thus, the signal yielded by subtraction unit 404 primarily includes content related to heart sounds.

The signal from the subtraction unit 404 is passed to an S1 isolator unit 406, which functions to achieve the result described with reference to operation 204 in FIG. 2. An exemplary method for automatically processing accelerometer signals to isolate S1, S2, and S3 heart sounds is disclosed in U.S. Pat. No. 5,792,195, issued to Carlson et al. on Aug. 11, 1998, which is incorporated by reference herein in its entirety.

The output of the S1 isolator unit 406 is a set of time-sequenced data representing an S1 heart sound. Such data is passed to a minima/maxima extractor 408 to find the global minima and maxima of the S1 complex, as described with reference to operation 206 in FIG. 2.

Finally, the output of the minima/maxima extractor 408 is passed to a median calculator 410 to find the median minima and median maxima exhibited by the last N S1 heart sounds, as described with reference to operations 208 and 210 in FIG. 2.

Returning briefly to FIG. 1, a formula presented therein describes a linear regression of the data contained in the graph. (In the case of the data presented in FIG. 1, the formula is y=0.00009x−0.0625). The "reliability" of the linear regression is indicated by $R^2$, which is a measure of the variance explained by the regression model (in the case of the data presented in the graph of FIG. 1, $R^2$=0.9866). In one example, the reliability of the data is improved (and therefore the reliability of the linear regression model, as understood by $R^2$ is improved) by performing the data processing schemes of FIGS. 2-4 upon heart sounds obtained during periods of exhalation; accelerometer data obtained from heart sounds occurring during periods of inhalation is ignored. To distinguish periods of exhalation and inhalation, transthoracic impedance may be examined (transthoracic impedance may decrease during exhalation, for example).

Figure 5:
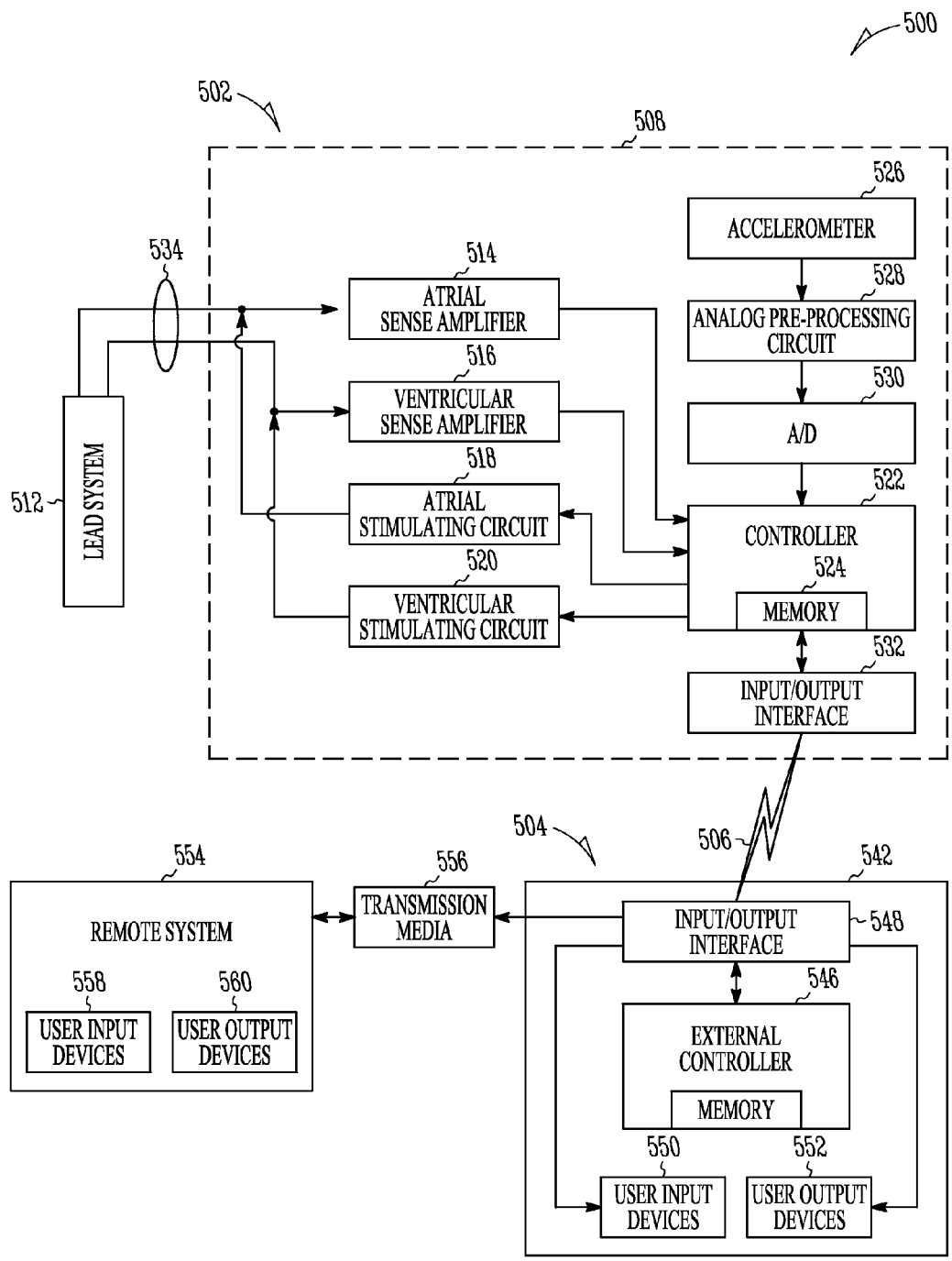
FIG. 5 depicts an exemplary system for performance of the methods and schemes disclosed herein.

FIG. 5 depicts an exemplary system useful for detecting S1 heart sounds, and extracting therefrom one or more morphological characteristics related to left ventricular contractility.

In FIG. 5, an exemplary system 500 for detecting and processing heart sounds includes an implantable system 502 and an external system 504. The implantable system 502 and external system 504 are configured to communicate via a communications link 506.

The implantable system 502 includes an implantable device 508 operatively coupled to a patient's heart by a lead system 512. The components of the implantable device 508 include an atrial sense amplifier 514, a ventricular sense amplifier 516, an atrial stimulating circuit 518, a ventricular stimulating circuit 520, a controller 522, a memory 524, an accelerometer 526, an analog pre-processing circuit 528, an analog-to-digital (A/D) converter 530, and an input/output (I/O) interface 532. The components of implantable device 508 are housed within an implantable housing (indicated by the broken lined box in FIG. 5), which may be implanted within the patient's chest cavity (e.g., in the pectoral region) or elsewhere.

The atrial sense amplifier 514, ventricular sense amplifier 516, atrial stimulating circuit 518 and ventricular stimulating circuit 520 are operatively coupled to lead system 512 via a pair of conductors 534. The lead system 512 may include an atrial sensing electrode and an atrial stimulating electrode adapted to be disposed in the right atrial chamber of heart and a ventricular sensing electrode and a ventricular stimulating electrode adapted to be disposed in the right ventricular chamber of the heart.

Sensed atrial and ventricular electrical signals generated by the sensing electrodes are applied to the atrial and ventricular sense amplifiers 514 and 516, respectively. Similarly, atrial and ventricular stimulating signals generated by the atrial and ventricular stimulating circuits 518 and 520 are applied to the atrial and ventricular stimulating electrodes, respectively. The atrial sense amplifier 514, ventricular sense amplifier 516, atrial stimulating circuit 518, and ventricular stimulating circuit 520, are each also operatively coupled to the controller 522.

In other embodiments, other sensing electrode configurations are used for internally sensing one or more electrical signals of heart. In one example, only one sensing electrode may be used. Alternatively, one or more electrodes placed within the body but outside of the heart are used for sensing cardiac electrical signals. In yet another example, a sensing electrode is placed on the implantable housing. In each of these examples, the sensing electrodes are operatively coupled to the controller 522.

In the embodiment shown in FIG. 5, the sensing electrodes and the stimulating electrodes are disposed in the right side of heart. In other embodiments, one or more sensing electrode(s) and one or more stimulating electrode(s) are disposed in the left side of the heart (in lieu of being disposed in the right side of the heart, or in addition to sensing electrode(s) and stimulating electrode(s) disposed in the right side of the heart). The addition of left heart sensing may advantageously allow for the resolution of ambiguities due to disassociation of right and left heart conduction.

The controller 522 includes a microcontroller or microprocessor which is configured to execute a program stored in a read-only memory (ROM) portion of a memory unit 524, and to read and write data to and from a random access memory (RAM) portion of the memory unit 524. By executing the program stored in memory 524, the controller 522 is configured to process the atrial and ventricular electrical signals from the atrial and ventricular sense amplifiers 514 and 516, and to provide control signals to the atrial and ventricular stimulating circuits 518 and 520. In response, the stimulating circuits 518 and 520 provide stimulating pulses to heart via atrial and ventricular stimulating electrodes at appropriate times. In other embodiments, the controller 522 may include other types of control logic elements or circuitry.

The implantable device 508 may be referred to as a dual-chamber pacemaker since pacemaking functions are provided to both atrial and ventricular chambers of heart. In another embodiment, the implantable system includes a single-chamber pacemaker that senses electrical signals and provides stimulating pulses to a single chamber of heart. In yet another embodiment, the implantable system does not provide any stimulation of heart tissues, but includes one or more sensing electrodes for sensing one or more electrical signals of heart, and for providing corresponding sensed signals to controller 522. In still another embodiment, the implantable system does not provide any sensing electrodes for sensing any cardiac electrical signals, but is configured to sense and transmit signals representing heart sounds using a sensor such as the accelerometer 526, as described below.

In the remainder of this description, the implantable device 508 is described as a dual-chamber pacemaker for the sake of illustration. It is to be understood, however, that implantable system 502 need not provide the stimulation functions described herein, and may provide other functions which are not described herein.

In some embodiments, a minute ventilation output channel and a minute ventilation input channel may be interposed between the controller 522 and the ventricular lead. The minute ventilation output channel generates a high-frequency, low-voltage signal that is transmitted from the ventricular lead (in either unipolar or bipolar mode). The input channel receives and conditions the signal. The content of the conditioned signal reveals respiration information.

An accelerometer 526 may be configured to provide sensed signals to the analog pre-processing circuit 528, which generates an analog output signal which is digitized by A/D converter 530. The digitized accelerometer signal is received by the controller 522. In the embodiment of FIG. 5, the accelerometer 526 is located within the housing of implantable device 508. In another embodiment, the accelerometer 526 is located on the housing of the implantable device. The accelerometer 526 may include, for example, a piezo-electric crystal accelerometer sensor of the type used by pacemakers to sense the level of activity of the patient, or may include other types of accelerometers. To detect heart sounds, other types of sound-detecting sensors or microphones may also be used, such as a pressure sensor or a vibration sensor configured to respond to sounds made by the heart.

In another embodiment, the system 500 includes two or more sound-detecting sensors. In such an embodiment, the plurality of sensed heart sound signals from the plurality of sensors may be individually transmitted to external system 504 for display as individual traces, may be combined (e.g., averaged) by external system 504 before being displayed as a single trace, or may be combined by controller 522 before being transmitted to external system 504 as a single heart sound signal. These sensors may include different types of sensors, sensors that are located in different locations, or sensors that generate sensed signals which receive different forms of signal processing.

In one embodiment, the accelerometer 526 is configured to generate sensed signals representative of two distinct physical parameters: (1) the level of activity of the patient; and (2) the heart sounds generated by heart. Accordingly, the analog pre-processing circuit 528 is configured to pre-process the sensed signals from the accelerometer 526 in a manner which conforms to the signal characteristics of both of these physical parameters. For example, if the frequencies of interest for measuring the patient's level of activity are below 10 Hz, while the frequencies of interest for detecting heart sounds are between 0.05 Hz and 50 Hz, then analog pre-processing circuit 528 may include a low-pass filter having a cutoff frequency of 50 Hz. The controller 522 may then perform additional filtering in software, as described above with reference to FIGS. 2-4, for example. Along with filtering, analog pre-processing circuit 528 may perform other processing functions including automatic gain control (AGC) functions.

The analog pre-processing circuit 528 may perform the filtering and baseline wander removal functions described with reference to operation 202 (FIG. 2) and may include modules 400, 402, and 404 (shown in FIG. 4). Alternatively, the analog pre-processing circuit 528 may simply provide automatic gain control functionality.

In some embodiments, the controller 522 performs one or more of steps 204-212 (FIG. 2), and may include one or more of modules 406-410 (FIG. 4). In the context of an embodiment in which the analog pre-processing circuit 528 performs only automatic gain control, the controller may perform operations 200 and 202 (FIG. 2), and may include modules 400-404 (FIG. 4). As discussed below, any operations 200-212 or modules 400-410 to be performed digitally by a controller may be performed cooperatively by the controller 522 within the implantable device 508 and another controller. For example, the controller 522 in the implantable device 508 may perform operation 204, and communicate the result to an external controller (contained in a programmer, for example) that performs operation 206-212. Alternatively, an external controller may perform all of the operations 200 described in FIG. 2.

In another embodiment, the implantable device 508 has two pre-processing channels for receiving sensed signals from accelerometer 526. In still another embodiment, implantable device 508 includes two accelerometers, with one accelerometer configured to generate sensed signals representative of the level of activity of the patient and the other accelerometer configured to generate sensed signals representative of heart sounds. In these latter two embodiments, any hardware and/or software processing performed on the sensed signals can conform to the specific characteristics of the respective sensed signals. For example, the analog pre-processing circuit used for the level-of-activity sensed signals can provide a low-pass filter with a cutoff frequency of 10 Hz, while the analog preprocessing circuit for the heart-sound sensed signals can provide a band-pass filter with cutoff frequencies of 0.05 and 50 Hz. In the latter case, each accelerometer can be selected, located and/or oriented to maximize the detection of the respective physical parameter. In yet another embodiment, if the implantable device does not need to sense the level of activity of the patient, the accelerometer 526 may measure only the sounds made by heart.

The controller 522 is capable of bi-directional communications with an external system 504 via an I/O interface 532. In one embodiment, the I/O interface 532 communicates using RF signals, which may be understood to include inductive coupling. In other embodiments, the I/O interface 532 communicates using optical signals, or a combination of RF and optical signals (e.g., RF signals for receiving data from the external system 504 and optical signals for transmitting data to external system 504, or vice-versa). The controller 522 uses the I/O interface 532 for bi-directional communications with the external system 504 to support conventional monitoring, diagnostic and configuration pacemaker functions. The controller 522 may also use the I/O interface 532 to telemeter data representative of the heart sounds sensed by accelerometer 526 to the external system 504. In various embodiments, the controller 522 further uses the I/O interface 532 to telemeter data representative of cardiac electrical signals (i.e., electrogram or EGM signals), which may include data representative of atrial electrical signals, sensed by the atrial sensing electrode, and/or data representative of ventricular electrical signals, sensed by the ventricular sensing electrode. Thus, implantable system 502 is capable of sensing heart sounds, atrial electrical signals and ventricular electrical signals, and of telemetering data representative of the heart sounds and/or cardiac electrical signals to external system 504. In other embodiments, the controller 522 telemeters data representative of cardiac electrical signals which were sensed by other configurations of internal cardiac sensing electrodes.

The external system 504 may include an external device 542. The external device 542 may include an external controller 546, an I/O interface 548, user input device(s) 550, and user output device(s) 552. Using the I/O interface 548, the external controller 546 is configured for bi-directional communications with the implantable device 508, for receiving input signals from input device(s) 550, and for applying control signals to output device(s) 552. The input device(s) 550 include at least one input device which allows a user (e.g., a physician, nurse, medical technician, etc.) to generate input signals to control the operation of external device 542, such as at least one user-actuatable switch, knob, keyboard, pointing device (e.g., mouse), touch-screen, voice-recognition circuit, etc. The output device(s) 552 include at least one display device (e.g., CRT, flat-panel display, etc.), audio device (e.g., speaker, headphone), or other output device which generates user-perceivable outputs (e.g., visual displays, sounds, etc.) in response to control signals. The external controller 546 may be configured to receive the data representative of heart sounds, atrial electrical signals and/or ventricular electrical signals from implantable system 502, and to generate control signals that, when applied to output device(s) 552, cause the output device(s) to generate outputs that are representative of the heart sounds, the atrial electrical signals and/or the ventricular electrical signals.

The external controller 546 may cooperate with the internal controller 522 to perform any or all of the steps in FIG. 2. For example, the implantable device 508 may telemeter conditioned accelerometer data (yielded from operation 202 in FIG. 2) to the external controller 546 via the communication link 506. The external controller 546 may perform operations 204-212 upon the telemetered data.

In one embodiment, the system 500 further includes a remote system 554 operatively coupled to communicate with the external system 504 via transmission media 556. The remote system 554 includes one or more user input device(s) 558, and one or more user output device(s) 560, which allow a remote user to interact with remote system 554. The transmission media 556 includes, for example, a telephone line, electrical or optical cable, RF interface, satellite link, local area network (LAN), wide area network (WAN) such as the Internet, etc. The remote system 554 cooperates with external system 504 to allow a user located at a remote location to perform any of the diagnostic or monitoring functions that may be performed by a user located at external system 504. For example, data representative of heart sounds and/or cardiac electrical signals are communicated by the external system 504 to the remote system 554 via the transmission media 556 to provide a visual display and/or an audio output on the output device(s) 560, thereby allowing a physician at the remote location to aid in the diagnosis of a patient. The system 554 is "remote" in the sense that a user of remote system 554 is not physically capable of actuating input device(s) 550 and/or of directly perceiving outputs generated by output device(s) 552. For example, the system 554 may be located in another room, another floor, another building, another city or other geographic entity, across a body of water, at another altitude, etc., from the external system 504.

Although not depicted in FIG. 5, the I/O interface 532 may establish a communication link with a communication device in physical proximity to the patient. For example, the I/O interface may establish a data link with a personal digital assistant, and may upload or download any of the data mentioned previously or hereafter. The personal digital assistant may, in turn, establish a link with an access point, so that the link may be effectively extended over a network, such as the Internet.

To this point, the disclosure has discussed schemes for detecting a heart sound, generating morphological data from the heart sound, and relating the morphological data to a hemodynamic metric (FIGS. 1-4). The disclosure has also discussed an exemplary device and system for performing such acts (FIG. 5). The remainder of the disclosure relates to methods which may make use of the methods discussed with reference to FIGS. 1-4, and may make use of the exemplary device or system disclosed with reference to FIG. 5.

Figure 6:
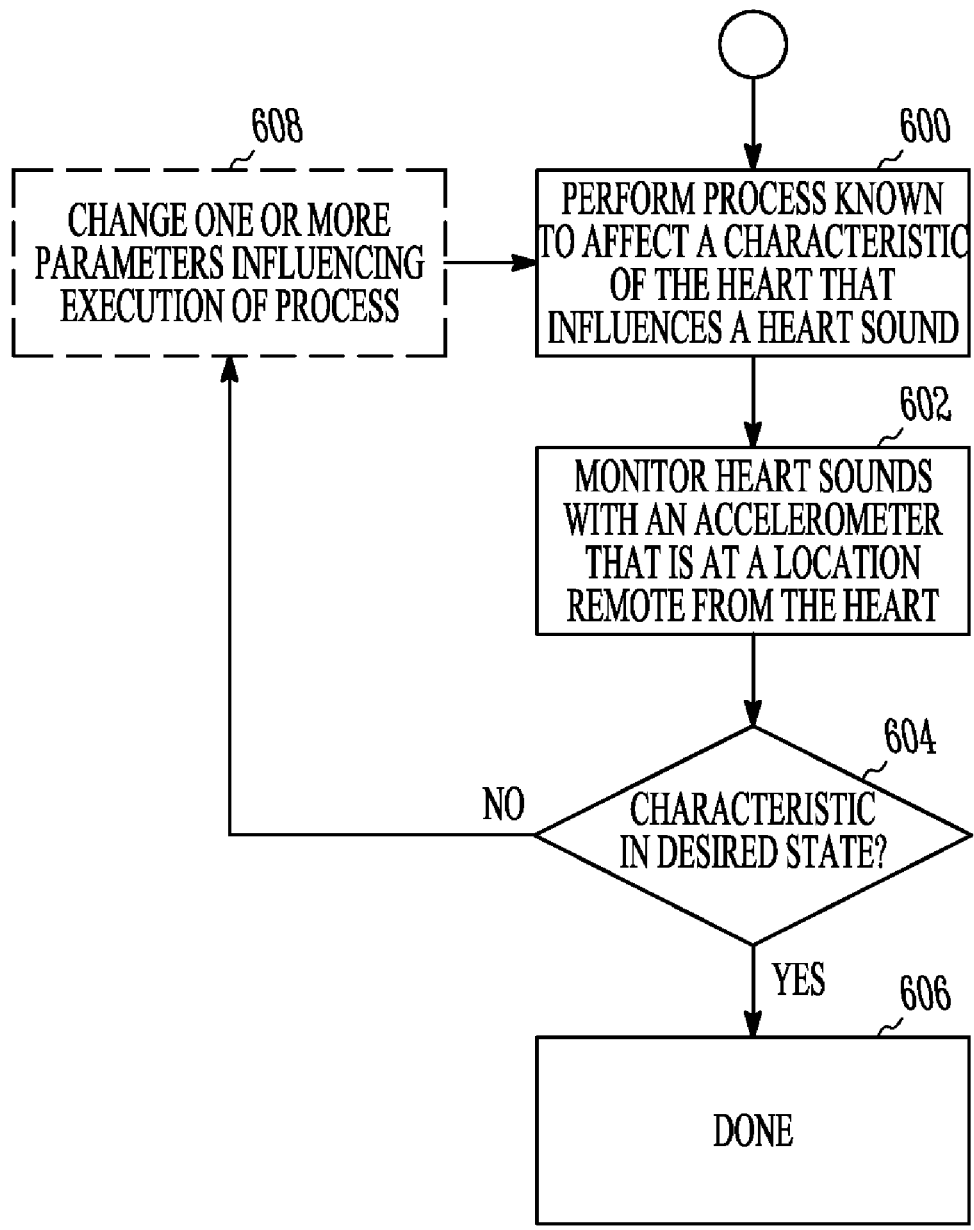
FIG. 6 depicts a method of adjusting parameters that influence a process, according to some embodiments of the present invention.

FIG. 6 depicts a method of adjusting parameters that influence a process. Any of the acts depicted in FIG. 6 may be performed by any controller in the exemplary system of FIG. 5. The method begins with performing a process known to affect a characteristic of the heart that influences sound, as shown in operation 600. For example, operation 600 may include titration of a drug known to influence a heart sound. An inotrope, for instance, enhances the inotropic state of the heart, resulting in greater myocardial contractility, which influences the S1 heart sound (as shown in FIG. 1). Alternatively, operation 600 may include administration of therapy to the heart. For instance, an implantable device (such as the one shown in FIG. 5) may administer cardiac resynchronization therapy to the heart. Over time, cardiac resynchronization therapy may make the heart stronger, resulting in greater myocardial contractility. Again, contractility is known to influence the S1 heart sound.

Next, in operation 602, the heart sounds are detected using an accelerometer that is located at a point that is remote from the heart (e.g., within an implantable device, such as the one depicted in FIG. 5). The monitoring operation 602 may include, for example, performing the acts discussed with reference to FIGS. 2-4. Thus, the median peak-to-peak amplitude exhibited by S1 heart sounds may be monitored (after being conditioned, as discussed with reference to FIGS. 2-4) to obtain information regarding the contractility of the left ventricle.

After monitoring the heart sounds in operation 602, it is determined whether the cardiac characteristic known to relate to the heart sound is in the desired state. For example, in the context of monitoring S1 heart sounds during administration of cardiac resynchronization therapy, the goal may be to increase or maximize contractility of the heart by administration of such therapy. Accordingly, operation 604 may involve a determination of whether the contractility of the heart has been maximized or sufficiently increased. If it is determined that the given cardiac characteristic (e.g., contractility) is, indeed, in the desired state, then the process may come to an end, as shown in operation 606. On the other hand, if the desired state has not been reached then control may be passed to operation 608.

Operation 608, is optional. In operation 608, one or more parameters influencing execution of the process of operation 600 are changed. For example, if operation 600 involved administration of cardiac resynchronization therapy, then one or more resynchronization parameters may be changed in operation 608. For example, an atrioventricular pacing delay parameter, biventricular delay parameter, electrode site selection parameter, etc. may be altered. Execution of operation 608 may be performed automatically by an implanted cardiac rhythm management device. Alternatively, it may be performed automatically by an external processor (e.g., accelerometer data is telemetered to a programmer or other external device; the accelerometer data is processed according to FIG. 2; the programmer automatically determines how to adjust one or more parameters on the basis of such processing, and new parameters are telemetered to the implantable device). Operation 608 may be performed manually as well (e.g., accelerometer data is telemetered to a programmer; the accelerometer data is processed according to FIG. 2; a health care professional analyzes the accelerometer data to determine how to adjust one or more parameters, and new parameters are telemetered to the implantable device). After execution of operation 608, control returns to operation 600, and the controlled process continues.

Operation 608 may be omitted entirely. For example, in the context of titration, rather than increasing or decreasing the titration rate in operation 608, the titration rate may remain constant, meaning that control returns to operation 600 and titration simply continues.

Thus, in sum, the loop defined by operations 600, 602, 604, and 608, functions to monitor and control a process, until a cardiac characteristic is observed (by virtue of detection of heart sounds with a remote accelerometer) to be in a desired state.

Figure 7:
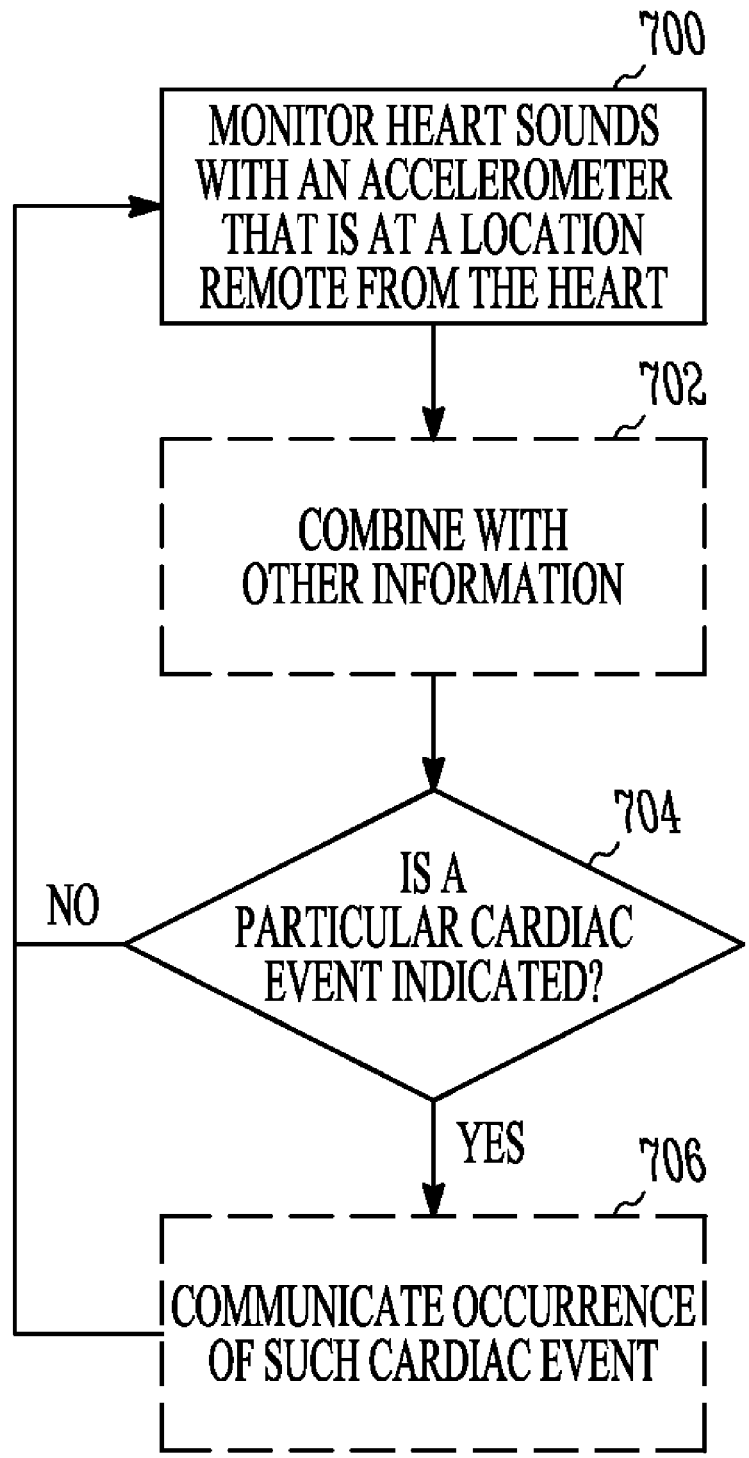
FIG. 7 depicts a method of identifying occurrence of a cardiac event, according to some embodiments of the present invention.

FIG. 7 depicts a method of identifying an occurrence of a cardiac event. Any of the acts depicted in FIG. 7 may be performed by any controller in the exemplary system of FIG. 5. The method begins with detecting heart sounds using an accelerometer that is located at a point that is remote from the heart (e.g., within an implantable device, such as the one depicted in FIG. 5), as shown in operation 700. The monitoring operation of operation 700 may include, for example, performing the acts discussed with reference to FIGS. 2-4. Thus, the median peak-to-peak amplitude exhibited by S1 heart sounds may be monitored (after being conditioned, as discussed with reference to FIGS. 2-4) to obtain information regarding the contractility of the left ventricle.

Thereafter, control may be passed to operation 702. Operation 702 is optional, and may be omitted altogether. In operation 702, the information obtained by monitoring of heart sounds in operation 700 is combined with other information (e.g., exertion level as indicated by rate of respiration and/or motion-related acceleration, etc.). The heart sound information may be combined with any of the information normally measured by a cardiac rhythm management device, for example.

Next, in operation 704, the information obtained from operations 700 and 702 (if performed) is analyzed to determine whether a cardiac event of interest is occurring. For example, the information may be analyzed to determine whether ischemia or acute heart failure decompensation is being exhibited by a patient. If no such event is detected, control is returned to operation 700, and the monitoring continues. On the other hand, if such an event is detected, control is passed to operation 706.

Operation 706 is optional. In operation 706, occurrence of the detected event is communicated. The communication may occur between an implanted cardiac management device (performing operations 700-706) and a programmer, a personal digital assistant, an access point to a network, such as a wireless or wired network, or to a wireless communication device that may forward the message to an access point for communication to a remote computing system, for example. (The programmer or personal digital assistant may relay such a message to a remote computing). Alternatively, the communication may occur between the detection routine executing on the internal controller and a history logging routine executed by the same internal controller. Thus, the occurrence of the detected event is logged, so that a health care professional may become aware of the event, for example, the next time he or she reads the data contained in the log. After execution of operation 706, control is returned to operation 700, and monitoring continues.

The method of FIG. 7 may be performed continually or at intervals. For example, a patient may be monitored for a given cardiac condition once per day (e.g., at night) or several times each day, meaning that the method of FIG. 7 would be executed once per day or several times per day.

Embodiments of the invention may be implemented in one or a combination of hardware, firmware, and software. Embodiments of the invention may also be implemented as instructions stored on a machine-readable medium, which may be read and executed by at least one processor to perform the operations described herein. A machine-readable medium may include any mechanism for storing or transmitting information in a form readable by a machine (e.g., a computer). For example, a machine-readable medium may include read-only memory (ROM), random-access memory (RAM), magnetic disc storage media, optical storage media, flash-memory devices, electrical, optical, acoustical or other form of propagated signals (e.g., carrier waves, infrared signals, digital signals, etc.), and others.

The Abstract is provided to comply with 37 C.F.R. Section 1.72(b) requiring an abstract that will allow the reader to ascertain the nature and gist of the technical disclosure. It is submitted with the understanding that it will not be used to limit or interpret the scope or meaning of the claims.

In the foregoing detailed description, various features are occasionally grouped together in a single embodiment for the purpose of streamlining the disclosure. This method of disclosure is not to be interpreted as reflecting an intention that the claimed embodiments of the subject matter require more features than are expressly recited in each claim. Rather, as the following claims reflect, inventive subject matter lies in less than all features of a single disclosed embodiment. Thus, the following claims are hereby incorporated into the detailed description, with each claim standing on its own as a separate preferred embodiment.

The claimed invention is:

1. A device comprising:
 a transducer configured to convert an acceleration correlative to a S1 heart sound into an electrical signal;
 a control circuit coupled to the transducer, the control circuit configured to receive the electrical signal, identify the acceleration correlative to the S1 heart sound, determine a maximum amplitude of the acceleration correlative to the S1 heart sound and a minimum amplitude of the acceleration correlative to the S1 heart sound, and determine a patient status indicator using an indication of a peak-to-peak difference between the maximum amplitude of the acceleration correlative to the S1 heart sound and the minimum amplitude of the acceleration correlative to the S1 heart sound, wherein the patient status indicator indicates at least one of contractility or a maximum time rate of change of pressure within a ventricle of a heart during a cardiac cycle, wherein the device is configured to detect an auxiliary physiological signal in conjunction with detection of the acceleration correlative to the S1 heart sound, the control circuit configured to use the auxiliary physiological signal in determining the patient status indicator, the auxiliary physiological signal including a motion-related acceleration.

2. The device of claim 1, wherein the device is configured to determine an auxiliary indicator using a characteristic of the auxiliary physiological signal; and wherein the control circuit is configured to:
   use the auxiliary indicator in determining the patient status indicator; and
   provide the patient status indicator for a user or automated process.

3. The device of claim 1, wherein the device is configured to detect respiration, the control circuit being configured to ignore, for purposes of determining the patient status indicator, an acceleration correlative to a S1 heart sound during a period of inhalation.

4. The device of claim 1, wherein the control circuit is configured to determine the peak-to-peak difference between the maximum amplitude of the acceleration correlative to the S1 heart sound and a minimum amplitude of the acceleration correlative to the S1 heart sound by:
   identifying a time, $t_m$, associated with a beginning of the acceleration correlative to the S1 heart sound, and a time, $t_n$, associated with an ending of the acceleration correlative to the S1 heart sound;
   identifying, during a span of time between $t_m$ and $t_n$, a global maximum amplitude of the acceleration correlative to the S1 heart sound and a global minimum amplitude of the acceleration correlative to the S1 heart sound;
   determining, for a plurality of accelerations correlative to respective S1 heart sounds, a central tendency of the global maximum amplitudes correlative to the respective S1 heart sounds and a central tendency of the global minimum amplitudes correlative to the respective S1 heart sounds; and
   subtracting the central tendency of the global minimum amplitudes correlative to the respective S1 heart sounds from the central tendency of the global maximum amplitudes correlative to the respective S1 heart sounds to determine the peak-to-peak difference.

5. The device of claim 1, wherein the control circuit is included with an external system, the control circuit being communicatively coupled with the transducer.

6. The device of claim 1, further comprising a therapy delivery circuit coupled to the control circuit, the therapy delivery circuit configured to deliver therapy to a heart in the form of electrical impulses.

7. The device of claim 6, wherein the control circuit is configured to adjust, using the patient status indicator, the therapy delivered by the therapy delivery circuit.

8. The device of claim 1, wherein the transducer comprises an accelerometer.

9. A method comprising:
   using a transducer to detect an acceleration correlative to an S1 heart sound;
   converting the acceleration correlative to S1 heart sound into an electrical signal using the transducer;
   using the electrical signal to determine a maximum amplitude of the acceleration correlative to the S1 heart sound and a minimum amplitude of the acceleration correlative to the S1 heart sound;
   determining a patient status indicator using an indication of a peak-to-peak difference between the maximum amplitude of the acceleration correlative to the S1 heart sound and the minimum amplitude of the acceleration correlative to the S1 heart sound, wherein the patient status indicator indicates at least one of contractility or a maximum time rate of change of pressure within a ventricle of a heart during a cardiac cycle; and
   detecting an auxiliary physiological signal in conjunction with detection of the acceleration correlative to the S1 heart sound, the auxiliary physiological signal being used in determining the patient status indicator, wherein the auxiliary physiological signal includes a motion-related acceleration.

10. The method of claim 9, comprising:
    determining an auxiliary indicator using a characteristic of the auxiliary physiological signal;
    using the auxiliary indicator in determining the patient status indicator; and
    providing the patient status indicator for a user or automated process.

11. The method of claim 9, comprising detecting respiration and ignoring, for purposes of determining the patient status indicator, an acceleration correlative to a S1 heart sound during a period of inhalation.

12. The method of claim 9, comprising determining the peak-to-peak difference between the maximum amplitude of the acceleration correlative to the S1 heart sound and the minimum amplitude of the acceleration correlative to the S1 heart sound by:
    identifying a time, $t_m$, associated with a beginning of the acceleration correlative to the S1 heart sound, and a time, $t_n$, associated with an ending of the acceleration correlative to the S1 heart sound;
    identifying, during a span of time between $t_m$ and $t_n$, a global maximum amplitude of the acceleration correlative to the S1 heart sound and a global minimum amplitude of the acceleration correlative to the S1 heart sound;
    determining, for a plurality of accelerations correlative to respective S1 heart sounds, a central tendency of the global maximum amplitudes correlative to the respective S1 heart sounds and a central tendency of the global minimum amplitudes correlative to the respective S1 heart sounds; and
    subtracting the central tendency of the global minimum amplitudes correlative to the respective S1 heart sounds from the central tendency of the global maximum amplitudes correlative to the respective S1 heart sounds to determine the peak-to-peak difference.

13. The method of claim 9, comprising storing the maximum amplitude of the acceleration correlative to the S1 heart sound and the minimum amplitude of the acceleration correlative to the S1 heart sound in a datastore, so that a trend regarding the maximum amplitude and the minimum amplitude may be obtained.

14. The method of claim 9, comprising adjusting, using the patient status indicator, a therapy delivered to the heart.

15. The method of claim 14, wherein the therapy comprises cardiac resynchronization therapy.

16. The method of claim 9, comprising adjusting a drug dosage using the patient status indicator.

17. A non-transitory device-readable medium including instructions that, when performed by the device, comprise:
    using a transducer to detect an acceleration correlative to an S1 heart sound;
    converting the acceleration correlative to S1 heart sound into an electrical signal using the transducer;
    using the electrical signal to determine a maximum amplitude of the acceleration correlative to the S1 heart sound and a minimum amplitude of the acceleration correlative to the S1 heart sound;

determining a patient status indicator using an indication of a peak-to-peak difference between the maximum amplitude of the acceleration correlative to the S1 heart sound and the minimum amplitude of the acceleration correlative to the S1 heart sound, wherein the patient status indicator indicates at least one of contractility or a maximum time rate of change of pressure within a ventricle of a heart during a cardiac cycle; and detecting an auxiliary physiological signal in conjunction with detection of the acceleration correlative to the S1 heart sound, the auxiliary physiological signal being used in determining the patient status indicator, wherein the auxiliary physiological signal includes a motion-related acceleration.

18. The non-transitory device-readable medium of claim 17, comprising:
   determining an auxiliary indicator using a characteristic of the auxiliary physiological signal;
   using the auxiliary indicator in determining the patient status indicator; and
   providing the patient status indicator for a user or automated process.

19. The non-transitory device-readable medium of claim 17, comprising detecting respiration and ignoring, for purposes of determining the patient status indicator, an acceleration correlative to a S1 heart sound during a period of inhalation.

20. The non-transitory device-readable medium of claim 17, comprising determining the peak-to-peak difference between the maximum amplitude of the acceleration correlative to the S1 heart sound and the minimum amplitude of the acceleration correlative to the S1 heart sound by:
   identifying a time, $t_m$, associated with a beginning of the acceleration correlative to the S1 heart sound, and a time, $t_n$, associated with an ending of the acceleration correlative to the S1 heart sound;
   identifying, during a span of time between $t_m$ and $t_n$, a global maximum amplitude of the acceleration correlative to the S1 heart sound and a global minimum amplitude of the acceleration correlative to the S1 heart sound;
   determining, for a plurality of accelerations correlative to respective S1 heart sounds, a central tendency of the global maximum amplitudes correlative to the respective S1 heart sounds and a central tendency of the global minimum amplitudes correlative to the respective S1 heart sounds; and
   subtracting the central tendency of the global minimum amplitudes correlative to the respective S1 heart sounds from the central tendency of the global maximum amplitudes correlative to the respective S1 heart sounds to determine the peak-to-peak difference.

* * * * *